US007312348B2

(12) United States Patent
McClain et al.

(10) Patent No.: US 7,312,348 B2
(45) Date of Patent: Dec. 25, 2007

(54) PROCESS FOR PREPARING SULFURIZED MOLYBDENUM DIALKYLDITHIOCARBAMATES

(75) Inventors: Keith Smith McClain, Murray, KY (US); Kenneth Barry Jolly, Benton, KY (US); Shaun Jeremy Ensor, East Haven, CT (US); Daniel Gershon, Terryville, CT (US); Robert John Tynik, Norwalk, CT (US); Clifford Dee Vail, Murray, KY (US); Stephen Gerard Wojtowicz, Shelton, CT (US)

(73) Assignee: R.T. Vanderbilt Company, Inc., Norwalk, CT (US)

( * ) Notice: Subject to any disclaimer, the term of this patent is extended or adjusted under 35 U.S.C. 154(b) by 0 days.

(21) Appl. No.: 11/736,251

(22) Filed: Apr. 17, 2007

(65) Prior Publication Data
US 2007/0249852 A1   Oct. 25, 2007

Related U.S. Application Data

(60) Provisional application No. 60/745,099, filed on Apr. 19, 2006.

(51) Int. Cl.
*C07F 11/00* (2006.01)
*C07F 13/00* (2006.01)
(52) U.S. Cl. .......................................... 556/50; 556/63
(58) Field of Classification Search .................. 556/50, 556/63
See application file for complete search history.

(56) References Cited

U.S. PATENT DOCUMENTS

| | | | |
|---|---|---|---|
| 3,356,702 A | 12/1967 | Farmer et al. | |
| 3,509,051 A | 4/1970 | Farmer et al. | |
| 4,098,705 A | 7/1978 | Sakurai et al. | |
| 4,846,983 A * | 7/1989 | Ward, Jr. ..................... | 508/363 |
| 5,627,146 A | 5/1997 | Tanaka et al. | |
| 2006/0199745 A1 | 9/2006 | Tynik et al. | |

* cited by examiner

*Primary Examiner*—Porfirio Nazario-Gonzalez
(74) *Attorney, Agent, or Firm*—Norris McLaughlin & Marcus PA

(57) ABSTRACT

A process is provided for the manufacture of highly sulfurized metal dithiocarbamates, such as molybdenum dithiocarbamate. A metal source source, water and a reagent amine are heated under pressure with carbon disulfide.

26 Claims, No Drawings

PROCESS FOR PREPARING SULFURIZED MOLYBDENUM DIALKYLDITHIOCARBAMATES

BACKGROUND OF THE INVENTION

The invention relates to a process for preparing highly sulfurized molybdenum dithiocarbamates. Conventional sulfurized molybdenum dithiocarbamates are known for use in lubricating formulations, and are currently used as additives in lubricating oils for imparting antifriction and antiwear properties, as well as extreme pressure and antioxidant properties. These compounds have the general structure $[R_1R^2N-CS-S]_2 \ Mo_2O_xS_{4-x}$, where x=2.35-3 and, therefore, are not highly sulfurized.

It is also known to increase the sulfur to oxygen in this structure $[R^1R^2N-CS-S]_2 \ Mo_2O_xS_{4-x}$, where x=0.75 to 2.1 and $R^1$ and $R^2$, which are the same or different, are hydrocarbyl groups containing 1 to 24 carbon atoms. Such higher sulfur compositions are prepared from a sulfide compound such as alkaline metal hydrogen sulfides, ammonium hydrogen sulfide, alkaline metal sulfides, ammonium sulfide and mixtures thereof as taught in U.S. Pat. No. 4,098,705.

There is a desire for the dithiocarbamates to have higher sulfur content (higher sulfurized). With sulfur being an antioxidant, these compounds have better antioxidant stability afforded by the increased sulfur content. Very high sulfur levels have been found to produce copper corrosion, but levels of up to about three sulfur atoms on the molybdenum core of structure $[R^1R^2N-CS-S]_2 \ Mo_2O_xS_{4-x}$, where $x \geq 1.0$, are acceptable. High sulfur content (wherein sulfur replaces oxygen) affords an internal antioxidant at the molecular level, which provides an increased stability to the molecule, which is believed to afford improved antifriction retention properties in their application. The known preparation methods for the higher sulfurized molybdenum dithiocarbamates involve the use of hydrogen sulfide or other sulfide during preparation to exchange oxygen-bound molybdenum to sulfur-bound molybdenum. The drawback of this process is the use of hydrogen sulfide or sources thereof, e.g. alkaline metal sulfides, ammonium sulfide and alkaline metal hydrogen sulfides, due to the danger and difficulty of handling these highly toxic materials.

SUMMARY OF THE INVENTION

The invention is an improved method to prepare high-sulfurized molybdenum dithiocarbamate compositions by using additional carbon disulfide in place of hydrogen sulfide (or a source thereof, e.g. sodium sulfide) as a sulfurization source. It has been unexpectedly discovered that under certain specific conditions, carbon disulfide can function as reagent that will sulfurize molybdenum dithiocarbamates, acting as a source to exchange oxygen bound to molybdenum with sulfur, with the production of carbon dioxide as the by-product. It is also expected that the process will prepare high-sulfurized dithiocarbamates of transition metals with valances of +3 or higher, such as tungsten, chromium, manganese, iron, cobalt, nickel, etc. The inventive process results in several important advantages over the prior art process: a simpler and safer process without the need to use $H_2S$ or sources thereof; a more economical process because less expensive $CS_2$ is used in place of $H_2S$ or sources thereof; and, as demonstrated below, a shorter total process time, at least with respect to liquid MoDTCs.

DETAILED DESCRIPTION OF THE INVENTION

Molybdenum dithiocarbamates are complexes of an inorganic core and dithiocarbamic acid. Bridged ("di-nulcear") or single molybdenum ("mono-nuclear") cores have been theorized. Additionally, coordination spaces on the molybdenum core may be filled with free amine or other coordinating moieties. This invention relates to a previously unknown method to prepare higher sulfurized versions of the existing dithiocarbamate technology. The precise structure of the resulting compounds is not known. However it is believed that the inventive compositions are molybdenum dithiocarbamates having the following general structure:

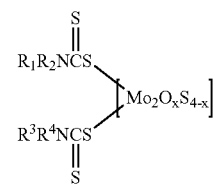

where $R^1$, $R^2$, $R^3$ and $R^4$ are independently selected from straight or branched chain, saturated or unsaturated alkyl groups from 1 to 40 carbon atoms, cycloalkyl groups of 6 to 40 carbon atoms, alkycycloalkyl groups of 7 to 40 carbon atoms, aryl groups of 6 to 40 carbon atoms, arylalkyl groups of 7 to 40 carbon atoms, where the alkyl groups may be substituted with heteroatoms or with other heteroatom-containing groups and x is a number from about 0.75 to about 2.1 The novel process for preparing higher-sulfurized molybdenum dialkyldithiocarbamates uses a molybdenum source, water, an optional inert organic solvent, carbon disulfide and one or more symmetric or asymmetric dialkylamines where $R^1$ and $R_2$ (and $R_3$ and $R_4$ in a case where two different amines are used) are either identical or dissimilar, or mixtures thereof. $R^1$, $R^2$, $R^3$ and $R^4$ are independently selected from straight or branched chain, saturated or unsaturated alkyl groups of 1 to 40 carbon atoms, cycloalkyl groups of 6 to 40 carbon atoms, alkylcycloalkyl groups of 7 to 40 carbon atoms, aryl groups of 6 to 40 carbon atoms, arylalkyl groups of 7 to 40 carbon atoms, where the alkyl and aryl groups may be substituted with heteroatoms or with other heteroatom-containing groups and preferably from branched or straight chain, saturated or unsaturated alkyl or heteroatom-containing alkyl groups containing 2 to 24 carbon atoms and more preferably containing 3 to 19 carbon atoms. For liquid MoDTCs, at least two of the four R groups $R^1$, $R^2$, $R^3$ and $R^4$ are preferably C8 to C19 and branched-chain to achieve higher oil solubility effects.

When using $CS_2$ as a sulfurizing source, the use of pressure during the reaction allows much higher reaction temperatures than would be obtainable at atmospheric pressure due to the low boiling point of $CS_2$, which in turn affords faster reaction. At lower temperatures, the $CS_2$ acts at such a slow rate as to be impractical. It only acts at a reasonable rate at temperatures well above its boiling point, typically at temperatures above about 93° C. (200° F.).

It has been found that the process for producing either a solid or a liquid product is best tailored accordingly, to provide optimized results for the particular product type (liquid or solid) desired. Therefore, the process details for each, although the same chemical conversion, are optimized to exploit production for the physical nature of the desired product (hereafter referred to as "liquid" or "solid" MoDTC) and are described separately.

In addition to the avoidance of $H_2S$ as a reactant, an important advantage of the present process is a reduced process time on a commercial scale for liquid DoDTCs. The commercial $H_2S$ process for a particular liquid MoDTC requires at least 10 hours for the addition of the $H_2S$ at the 1893 liters (500-gallon) scale and a estimated 16 hours or more at the 8328 Liter (2200-gallon) scale. The present process does generally have a 6-10 hour sulfurization reflux or heating period for liquid MoDTC, but this times does not increase with increases in scale. Therefore, the invention process is at least 6-10 hours shorter than the $H_2S$ process at the 8328 Liter (2200-gallon) scale for liquid MoDTC. The process time saved increases as the scale of the process increases.

The process details for liquid MoDTCs, using plant scale reactors, are given below:

Water, the reagent amine(s) and a molybdenum source (such as molybdenum trioxide, molybdic acid or ammonium molybdate and/or as taught by U.S. Pat. No. 5,494,608) are placed into a pressure reactor equipped with an automatic pressure relief valve (also know as automated pressure control valve). Ammonium molybdate can be prepared in situ by the reaction of molybdenum trioxide or molybdic acid with aqueous ammonia. Starting with ammonium molybdate, either pre-made or made in situ, shortens the process some because the digestion of $MoO_3$ would not be needed. The mole ratio of reagent amine(s):molybdenum is in the range 1.0-2.1:1.0, but typically about 1.0-1.1:1.0, depending on the desired product. The amount of water will be known to those skilled in the art. In the case of using molybdenum trioxide, e.g., the amount of water can be approximately the same weight as the molybdenum trioxide, though slightly more or less would not affect the result. It is preferred that these reagents are heated together to digest the molybdenum source prior to addition of carbon disulfide, unless ammonium molybdate is used as the molybdenum source. The typical digestion temperature range is at reflux temperature (~99-104° C.) {~210-220° F.]. The most preferred digestion time is when all solids have dissolved (typically about 2-4 hours at a temperature of about (~99-104° C.) [210-220° F.].

It is preferably to remove the water from the reactor by distillation after the digestion is complete. If the reagent amine has low solubility in water, then any amine that distills over with the water can be separated from the water via the reactor decanter and returned to the reactor.

After the water has been removed, the reactor is cooled (typically to below 93° C. [200° F.]) and some process oil may be added if needed in order to reduce the viscosity for improved agitation. The reactor is then sealed, cooled to below 54° C. (130° F.) and evacuated. The carbon disulfide is then introduced. The mole ratio of carbon disulfide: molybdenum is about 2.1-3.5:1.0, preferably about 2.2-3.0: 1.0 and most preferred about 2.3-2.5:1.0. Reactor pressure initially increases from $CS_2$ vapor pressure, and then the pressure is maintained at a level sufficient to achieve a reflux temperature of about 107-1035° C. (225-275° F.). A reactor pressure sufficient to achieve the desired reflux temperatures (i.e. to achieve sulfurization) will be about 13790-275792 Pa $(N/m^2)$ [2-40 psi or psig], preferably about 34474-172370 Pa $(N/m^2)$ [5-25 psig], and most preferably about 48264-103422 Pa $(N/m^2)$ [7-15 psig]. Typically the conversion to high-sulfurized product is realized with a reflux period of about 6-10 hours. However, the use of higher pressures and temperatures than those given above will increase the sulfurization rate and allow the use of shorter reflux or heating times. The generation of $CO_2$ during sulfurization will cause the reactor pressure to increase, requiring the release of excess pressure to a caustic scrubber via the automatic pressure relief valve (also know as automated pressure control valve).

When the reflux period is complete, any un-reacted carbon disulfide is stripped off either while still under pressure or after the pressure has been released. This carbon disulfide is recovered and recycled into future batches.

Vacuum is then applied to the reactor and the product is heated to about 141-157° C. (285-315° F.) to remove any remaining traces of carbon disulfide and water.

Typically a brown product is desired for aesthetic reasons. Therefore, an optional step may be added to achieve this color change by heating until the appropriate color is achieved, so the product is heated at 141-157° C. (285-315° F.) under vacuum until it reaches the desired brown color (usually 2-4 hours). Additional process oil can now be added if needed to reduce the viscosity for easier product handling.

The process details for solid MoDTCs are given below:

Water, the reagent amine(s), a molybdenum source (such as molybdenum trioxide, molybdic acid or ammonium molybdate) and optionally, an inert organic solvent, are placed into a pressure reactor equipped with an automatic pressure relief valve (also know as automated pressure control valve). Ammonium molybdate can be prepared in situ by the reaction of molybdenum trioxide or molybdic acid with aqueous ammonia. Use of an optional solvent is a method for solid MoDTCs which allows filtration of the product and recycling of the solvent system and can offer improvements in handling of the solid product. The optional organic solvent can be an excess of the reagent amine(s), a non-reactive amine or various higher-boiling solvents, such as cellosolves, carbitols, diglyme, xylene, etc. The mole ratio of reagent amine(s):molybdenum is in the range 1.0-2.1:1.0, but typically about 1.0-1.1:1.0, depending on the desired product.

It is preferred that these reagents are heated together to digest the molybdenum source prior to addition of carbon disulfide, unless ammonium molybdate is used as the molybdenum source. The most preferred digestion time is ½ to 1 hours or until all solids have dissolved. The preferred temperature is 54-82° C. (130-180° F.).

The reactor is cooled to below 38° C. (100° F.) and sealed. Carbon disulfide is then introduced to the sealed reactor. The mole ratio of carbon disulfide:molybdenum is about about 2.1-3.5:1.0, preferably about 2.2-3.0:1.0 and most preferred about 2.3-2.5:1.0. The reactor temperature is then slowly increased over about two hours with the pressure-relief valve set to the maximum desired reactor pressure. The reaction mixture is heated to about 121-138° C. (250-280° F.) or reflux temperature under 13789-206844 Pa $(N/m^2)$ [20- 30 psi or psig} of pressure. Typically the conversion to high-sulfurized solid product is realized with a heating period of 8-13 hours. If required, pressures higher than 206844 Pa $(N/m^2)$ [30 psig] can be used to give higher temperatures, thus increasing the sulfurization rate and allowing the use of shorter heating times. The use of a high-boiling organic solvent, such as propyl cellosolve or excess reagent amine(s), will also increase reaction temperatures and increase the rate of sulfurization. The use of high-boiling solvents may allow the required sulfurization temperatures to be achieved without reflux. When the heating period is complete, any un-reacted carbon disulfide can be removed by first releasing the pressure on the reactor system and then atmospherically stripping the carbon disulfide up to about 66° C. (150° F.) . This carbon disulfide can be recovered and recycled into future batches. The product slurry is filtered and then the filter cake is washed and dried.

EXAMPLES

Liquid Product Examples

The results for eight batches are given in the table below. Batch 8 was a scaled down production batch. All 8 batches were made using bis($C_{11}$-$C_{14}$-branched and linear alkyl) amine, available from BASF Corporation as "ditridecylamine".

Solid Product Examples

A commercial solid MoDTC (Molyvan® A, available from R. T. Vanderbilt Company, Inc.) prepared without pressure contains predominately the lower sulfurized MoDTC compound as is shown in the table below. The lower sulfurized MoDTC compound is HPLC peak #1 and the higher sulfurized MoDTC compound is peak #2. Labo-

| | Batch | 1 | 2 | 3 | 4 | 5 | 6 | 7 | 8 |
|---|---|---|---|---|---|---|---|---|---|
| Charges | Amine (lbs) | 180 | 180 | 180 | 180 | 180 | 180 | 180 | 761 |
| | kgs | 81.6 | 81.6 | 81.6 | 81.6 | 81.6 | 81.6 | 81.6 | 345 |
| | $MoO_2$ (lbs) | 56.3 | 56.3 | 56.3 | 56.3 | 56.3 | 56.3 | 56.3 | 244 |
| | kgs | 25.5 | 25.5 | 25.5 | 25.5 | 25.5 | 25.5 | 25.5 | 111 |
| | Process Oil (lbs) | 280 | 280 | 280 | 280 | 280 | 280 | 280 | 1186 |
| | kgs | 127 | 127 | 127 | 127 | 127 | 127 | 127 | 538 |
| | $CS_2$ (lbs) | 85 | 94 | 94 | 94 | 94 | 74 | 74 | 313 |
| | kgs | 38.6 | 42.6 | 42.6 | 42.6 | 42.6 | 33.6 | 33.6 | 142 |
| Digestion | Hours | 4 | 4 | 4 | 4 | 4 | 4 | 4 | 4 |
| | Distillation | No | Yes | Yes | Yes | Yes | Yes | Yes | Yes |
| | First oil charge | 20% | 20% | 20% | 20% | 50% | 50% | 50% | 60% |
| $CS_2$ Hold | Hours | 11.5 | 12 | 12 | 2 | 0.25 | 2 | 1 | 0.75 |
| | Temp. (F.) | 108-117 | 136-151 | 120-163 | 131-179 | 130-188 | 122-171 | 122-212 | 121-196 |
| | (C.) | | | | | | | | |
| Reflux | Hours | 4.5 | 12 | 12 | 12 | 13 | 10 | 8 | 6 |
| | Temp. (F.) | 190-198 | 186-206 | 178-213 | 179-201 | 204-236 | 171-271 | 212-260 | 203-247 |
| | (C.) | 88-92 | 86-97 | 81-101 | 82-94 | 96-113 | 77-133 | 100-127 | 95-119 |
| | Pressure (psig) | 0 | ~10 | ~7-10 | ~10-14 | ~7-15 | ~9-15 | ~10-14 | ~10 |
| | Pa ($N/m^2$) | 0 | ~65948 | ~48264~68948 | ~68948~96527 | ~48264~103422 | ~62053~103422 | ~68946~96527 | ~96527 |
| Cook | Hours | 4 | 2.5 | 3 | 2.5 | 4 | 3 | 2.5 | 4 |
| | Temp. (F.) | 274-302 | 285-295 | 290-301 | 299-305 | 280-312 | 285-313 | 285-314 | 294-303 |
| | (C.) | 134-150 | 141-146 | 143-149 | 148-151 | 138-156 | 141-156 | 141-157 | 146-151 |
| | Color | green | brown | brown | brown | brown | brown | brown | brown |
| | Total product (lbs) | 535 | 544 | 524 | 481 | 539 | 540 | — | 2405 |
| | Kgs | 242.7 | 246.6 | 237.7 | 218.2 | 244.5 | 244.9 | — | 1090.9 |
| | Total time (hrs) | 30.8 | 38.3 | 38.5 | 25.5 | 29.5 | 24.5 | 23 | — |

| Batch | Visual Color | ASTM Color 1% in Hexane | Density @ 25° C. | % Hexane Insolubles | % Mo | IR | % S | Viscosity (cSt) | S/Mo Mole ratio |
|---|---|---|---|---|---|---|---|---|---|
| 1 | Green | L5.0 | 1.00 | 0.05 | 7.1 | OK | 4.6 | 17 | 1.9 |
| 2 | Brown | L3.0 | 0.99 | 0.033 | 6.9 | OK | 6.5 | 23 | 2.6 |
| 3 | Brown | L3.0 | 1.00 | 0.03 | 6.9 | OK | 6,7 | 22 | 2.9 |
| 4 | Brown | L5.0 | 0.99 | 0.137 | 6.8 | OK | 6.1 | 24 | 2.7 |
| 5 | Brown | L4.0 | 1.00 | 0.05 | 7.0 | OK | 6.6 | 23 | 2.8 |
| 6 | Brown | L4.0 | 1.00 | 0.023 | 6.9 | OK | 7.1 | 24 | 3.1 |
| 7 | Brown | L3.5 | 0.998 | 0.04 | 6.9 | OK | 6.3 | 22 | 2.7 |
| 8 | Brown | L2.5 | 0.994 | 0.09 | 6.6 | OK | 6.5 | 22 | 2.9 |
| Desired Specifications | Brown | 6.0 max. | 0.99-1.02 | 0.1% max. | 6.6-7.2 | Equal | 5.8-6.7 | 13-28 @ 100 C. | 2.4-3.0 | ratory batches 9-14 made by the invention process contain predominately the higher sulfurized MoDTC as is shown in the table below.

|  | Batch | MOLYVAN A | 9 | 10 | 11 | 12 | 13 | 14 |
|---|---|---|---|---|---|---|---|---|
| Charges (moles) | Molybdenum Trioxide | 1 | 1 | 1 | 1 | 1 | 1 | 1 |
|  | Water | 0 | 19.8 | 4.8 | 19.3 | 4.8 | 4.8 | 7.2 |
|  | Propyl Cellosolve | 0 | 0 | 3.4 | 2.3 | 3.4 | 3.4 | 0 |
|  | n-Propanol | 6.0 | 0 | 0 | 0 | 0 | 0 | 0 |
|  | Dibutylamine | 2.2 | 2.2 | 2.2 | 2.2 | 2.2 | 2.2 | 5 |
|  | Carbon Disulfide | 2.1 | 3 | 2.1 | 2.1 | 2.1 | 2.1 | 2.1 |
| Reaction | Hold | 1 | 2 | 0 | 0 | 0 | 0 | 0 |
|  | Reflux time (hrs.) | 8 | 13 | 8 | 13 | 13 | 13 | 13 |
|  | Reflux temp. (° C.) | 60-90 | 98-127 | 99-130 | 112-127 | 119-129 | 125-129 | 120-128 |
|  | Reflux pressure (psi) | 0 | 23-28 | 26-30 | 28-30 | 20-30 | 26-30 | 30 |
|  | Pa (N/m$^2$) | 0 | 158580-193054 | 179265-206844 | 193054-206844 | 137896-206844 | 179265-206844 | 208844 |
| Results HPLC | % Yield | 92-98 | 98.5 | 91.6 | 95.6 | 87 | 85.7 | 92.4 |
|  | Weight % S | 23.5-25.5 | 27.4 | 27.3 | 27.2 | 27.8 | 28.2 | 27.9 |
|  | Color | yellow | brown | brown | org/yellow | burnt org | yellow/org | org/yellow |
|  | Area % peak 1 | ~90 | 0.4 | 10.5 | 10.1 | 0.3 | 1 | 0 |
|  | Area % peak 2 | ~10 | 98.7 | 88.4 | 88.7 | 96.7 | 97.3 | 96.1 |

What is claimed is:

1. A method for preparing highly sulfurized metal dithiocarbamates, comprising the steps of:
   reacting a metal source, water, at least one reagent amine, and carbon disulfide, under pressure, at a temperature above the normal boiling point of carbon disulfide.

2. The method of claim 1, wherein the metal is a transition metal with valance of +3 or higher.

3. The method of claim 2, wherein the metal is molybdenum.

4. The method of claim 1, comprising the steps of, in order:
   heating together in a reactor the metal source, the water and the reagent amine at least such time as all solids have dissolved, and
   introducing into the reactor the carbon disulfide.

5. The method of claim 4, further comprising the step of, after the solids have dissolved, and prior to the introduction of carbon disulfide, removing the water from the reactor.

6. The method of claim 4, further comprising the step of, prior to the introduction of carbon disulfide, cooling the reactor contents.

7. The method of claim 4, for producing a liquid metal dithiocarbamate, further comprising the steps of, prior to the introduction of carbon disulfide, sealing the reactor, cooling the reactor contents to below 54° C. (130° F.) and evacuating the reactor.

8. The method of claim 4, for producing a solid metal dithiocarbamate, further comprising the steps of, prior to the introduction of carbon disulfide, sealing the reactor and cooling the reactor contents to below 37.8° C. (100° F.).

9. The method of claim 7, further comprising the steps of, prior to the sealing step, cooling the reactor contents to below 93.3° C. (200° F.) and adding process oil sufficient to reduce viscosity.

10. The method of claim 7, further comprising the step of, following the introduction of carbon disulfide, heating the reactor contents under pressure to achieve a desired reflux temperature at which a highly sulfurized metal dithiocarbamate is formed.

11. The method of claim 10, wherein the reflux temperature is about 107-135° C. (225-275° F.).

12. The method of claim 11, further comprising the step of, after completion of reflux, stripping off un-reacted carbon disulfide.

13. The method of claim 8, further comprising the step of, following the introduction of carbon disulfide, heating the reactor contents under pressure to achieve a desired reflux temperature at which a highly sulfurized metal dithiocarbamate is formed.

14. The method of claim 13, wherein the reflux temperature is about 121-138° C. (250-280° F.).

15. The method of claim 14, wherein the temperature of the reactor contents is slowly increased to reflux temperature over about 2 hours, with a pressure-release valve of the reactor set at the maximum desired pressure.

16. The method of claim 12, further comprising the step of, after stripping, applying a vacuum to the reactor and heating the reactor contents to about 141-157° C. (285-315° F.) to remove any remaining carbon disulfide and water.

17. The method of claim 13, further comprising the step of, after completion of reflux, stripping off un-reacted carbon disulfide.

18. The method of claim 3, wherein the molar ratio of reagent amine:molybdenum is about 1.0-2.1:1.0.

19. The method of claim 3, wherein the molar ratio or reagent amine:molybdenum is about 1.0-1.1:1.0.

20. The method of claim 4, wherein the molar ratio of carbon disulfide:molybdenum is about 2.1-3.5:1.0.

21. The method of claim 20, wherein the molar ratio of carbon disulfide:molybdenum is about 2.2-3.0:1.0.

22. The method of claim 21, wherein the molar ratio of carbon disulide:molybdenum is about 2.3-2.5:1.0.

23. The method of claim 3, wherein the molybdenum source is chosen from among molybdenum trioxide, molybdic acid and ammonium molybdate.

24. The method of claim 23, wherein the molybdenum trioxide.

25. The method of claim 1, wherein the reagent amine is chosen from one or more symmetric or asymmetric dialkylamines where $R_1$ and $R_2$, and $R_3$ and $R_4$ in a case where two different amines are used, are either identical or dissimilar, or mixtures thereof, and $R^1$, $R^2$, $R^3$ and $R^4$ are independently selected from straight or branched chain, saturated or unsaturated alkyl groups of 1 to 40 carbon atoms, cycloalkyl groups of 6 to 40 carbon atoms, alkylcycloalkyl groups of 7 to 40 carbon atoms, aryl groups of 6 to 40 carbon atoms, arylalkyl groups of 7 to 40 carbon atoms, where the alkyl and aryl groups may be substituted with heteroatoms or with other heteroatom-containing groups and preferably from branched or straight chain, saturated or unsaturated alkyl or heteroatom-containing alkyl groups containing 2 to 24 carbon atoms.

26. The method of claim 1, wherein an excess of carbon disulfide is added.

* * * * *